US00PP10072P

United States Patent [19]

Carruth

[11] Patent Number: Plant 10,072

[45] Date of Patent: Oct. 21, 1997

[54] FLORIBUNDA ROSE PLANT VARIETY NAMED 'WEKCRYPLAG'

[75] Inventor: Thomas F. Carruth, Altadena, Calif.

[73] Assignee: Weeks Wholesale Rose Grower, Inc., Upland, Calif.

[21] Appl. No.: 656,453

[22] Filed: May 31, 1996

[51] Int. Cl.[6] ..... A01H 5/00

[52] U.S. Cl. ..... Plt./26

[58] Field of Search ..... Plt./26, 22, 11, Plt./18

[56] References Cited

U.S. PATENT DOCUMENTS

P.P. 2,722 2/1967 Lammertz ..... Plt./26

*Primary Examiner*—Howard J. Locker

*Attorney, Agent, or Firm*—Christie, Parker & Hale, LLP

[57] ABSTRACT

A new plant variety of Floribunda rose suitable for garden decoration, having flowers of clear lavender coloration.

1 Drawing Sheet

BACKGROUND OF THE INVENTION

This invention relates to a new and distinct variety of Floribunda Rose. The varietal denomination of the new variety is 'Wekcryplag'. The new variety is bushy and upright and suitable for outdoor garden decoration. It has as its seed parent the variety known as 'Arobipy' (U.S. Plant Pat. No. 6,714) and as its pollen parent the variety known as 'Morplag' (U.S. Plant Pat. No. 6,468).

SUMMARY OF THE INVENTION

Among the features which distinguish the new variety from other presently available and known commercial rose cultivars are the following combination of characteristics: its semi-double flowers of clear lavender coloration, its very vigorous floriferous plant and its rounded plant habit. 'Wekcryplag' may be asexually propagated by cuttings, budding, and grafting.

Asexual reproduction of the new variety by budding as performed in Kern County and Upland, Calif., shows that the foregoing and other distinguishing characteristics come true to form and are established and transmitted through suceeding propagations.

Comparison with Parents

The new rose may be distinguished from its seed parent, 'Arobipy' (U.S. Plant Pat. No. 6,714), by the following combination of characteristics: whereas the seed parent bears very large double flowers of white coloration, 'Wekcryplag' bears significantly smaller semi-double flowers of a clear lavender coloration. 'Arobipy' has a tall upright plant habit, whereas the new variety has a significantly shorter more rounded plant habit. 'Wekcryplag' is classified as a Floribunda, whereas 'Arobipy' is classified as a Hybrid Tea.

The new variety may be distinguished from its pollen parent, 'Morplag' (U.S. Plant Pat. No. 6,468), by the following combination of characteristics: whereas the pollen parent bears flowers of a deep pink coloration, 'Wekcryplag' bears flowers of a light lavender coloration. 'Morplag' bears single petaled flowers (5 to 8 petals), whereas the new variety bears semi-double flowers with significantly more petals (12 to 16). 'Wekcryplag' has distinctive deep green foliage, whereas 'Morplag' has a significantly lighter green foliage.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of specimens of the new cultivar grown outdoors in Upland, Calif. in the month of October. Phenotypic expression may vary with environmental, cultural and climatic conditions, as well as differences in conditions of light and soil.

Flower

The new variety bears its flowers sometimes singly, usually in clusters of three or more per stem. Flowers are borne in irregular clusters on strong medium-to-long stems (about 22 to about 30 cm.) for the class. Outdoors the plant blooms abundantly and nearly continuously during the growing season. The flowers have a moderate fruity of apple-like fragrance.

Bud

The peduncle is of short-to-average length for the class (about 4 to about 5 cm.), of average caliper, and usually erect. It is moderately smooth with few stipitate glands. Peduncle color is between 144A and 138A.

Before the calyx breaks, the bud is of medium size for the class (about 2.2 to about 2.5 cm. in diameter at the widest point), moderately long in length (about 3.3 to about 3.9 cm.), and pointed to ovoid in shape. The surface of the bud bears few stipitate glands, usually with slender foliaceous parts extending beyond the tip of the bud equal to ¼or more of its length. Bud color is between 144A and 138A.

The inner surface of the sepals is covered and edged with fine wooly tomentum.

As the petals open, the bud is medium-to-large for the class (about 2.3 to about 2.6 cm. in diameter at the widest point), of moderately long length (about 3.5 to about 4.0 cm.), and very pointed to urn-shaped in form. The color of the under surfaces of the newly opened petals is between 68A and 73B. At the point where the petal attaches, there is small zone of near 1D coloration. The color of the upper rfaces of the newly opened petals is between 76A and C. At the point where the petal attaches, there is a very nall zone of near 5C coloration. The bud opens up well and generally not prevented from opening by wet, cold, hot or y weather.

Bloom

When fully open, the bloom is moderately large for the ass, ranging from about 10 to about 12 cm. in diameter. etalage is semi-double with about 12 to 16 petals and about to 2 petaloids arranged regularly. When partially open, the oom form is moderately high centered and the petals are omewhat cupped with petal edges slightly rolled outward. Then fully open, the bloom form is more flat-to-cupped and e petals are somewhat flat-to-undulated with petal edges ery slightly rolled outward.

Petals

The substance of the petals is somewhat heavy and oderately thick, with upper surfaces slightly satiny and nder surfaces somewhat shiny to satiny. The outer petals re nearly round to broadly obovate in shape with rounded pices. The inner petals are broadly obovate in shape with ounded apices.

Newly Opened Flower

The under surface of the outer and inner petals is between 8C and 73D. At the point where the petal attaches, there is small zone of near 2D coloration. The upper surface of the uter and inner petals is between 75C and 76B. At the point where the petal attaches, there is a very small zone of near 5C in coloration.

The general tonality of the newly opened flower is etween 75C and 76B.

Three Day Old Flower

The under surface of the outer and inner petals is between 58D and 73C. At the point where the petal attaches, there is a small zone of near 158D in coloration. The upper surface of the outer and inner petals is between 75D and 76C. At the point where the petal attaches, there is a very small zone of near 158D in coloration.

The general tonality of the three day old flower is between 75D and 76D.

On the spent bloom, the petals usually drop off cleanly.

In Upland, Calif., in October, blooms on the bush growing outdoors generally last from four to five days. Cut roses grown outdoors and kept at normal indoor living temperatures generally last from four to five or more days.

Male Reproductive Organs

Stamens are average to many in number and are arranged regularly about the pistil. The filaments are of medium to long length, many with anthers. The anthers are of medium size for the class and all open approximately at the same time. Anther color is near 17C when immature and near 165C at maturity. Pollen is very abundant and near 12C in color.

Female Reproductive Organs

Pistils vary in number (approximately 60). The styles are somewhat uneven, average to long in length, moderately thin in caliper, and loosly bunched. Stigma color is near 4B. Style color is 1C. Ovaries are usually all enclosed in the calyx.

Hips are average in length, globular in form, and near 25C in color when ripe. The hip surface is very smooth with thick fleshy walls. Seeds are average to many in number (approximately 18 to 24), and usually medium to large in size.

Foliage

The compoud leaves are usually comprised of three to five or more leaflets and are borne abundantly. The leaves are medium to large for the class (about 7 to about 12 cm. in length and about 7 to about 9 cm. in width at the widest point), moderately heavy in texture, and semi-glossy in finish. The leaflets are medium to large for the class (about 3 to about 5 cm. in length and about 1.9 to about 3.7 cm. in width at the widest point), oval to ovate in shape with moderately acute apices and rounded to acute bases. Their margins are usually doubly serrate.

The upper surface of the mature leaf is between 147A and 139A. The under surface of the mature leaf is between 191B and 138B. The upper surface of the young leaf is between 146A and 138A, usually suffused with between 187A and 183B. The under surface of the young leaf is near 146C, heavil suffused with between 187A and 183B.

The rachis is average to heavy in caliper and moderately rough. The upper side is moderately grooved with many large stipitate glands on the edges of the grooves. Sometimes the upper side is lightly suffused with near 183B. The under side of the rachis is moderately rough with some stipitate glands and prickles of varying sizes.

The stipules are medium in length and somewhat narrow in width with medium to long straight points that usually turn out an an angle of more than 45 degrees.

The plant displays an average degree of resistance to blackspot and rust as compared to other commercial varieties grown under comparable conditions in Upland, Calif.

Growth

The plant has a bushy upright medium height habit (about 90 to about 100 cm. in height and about 90 to about 120 cm. spread at the widest point in Upland, Calif., with very full branching. It displays very vigorous growth and the canes are of medium to heavy caliper for the class.

The color of the major stems is near 146C. They bear few large prickles which are medium length for the class (about 0.7 to about 1 cm.). The large prickles are almost straight angled slightly downward with a medium length broad base; prickle color is near to 165B. The major stem bears no small prickles.

The color of the branches is between 146B and 139A. They bear several large prickles which are of similar size and shape to the large prickles on the major stems; prickle color is near 161B. The branches bear no small prickles.

The color of the new shoots is between 138B and 144A often lightly suffused with between 187A and 138B. They bear several large prickles which are of similar size and shape to the large prickles on the major stems; prickle color is near 183B. The shoots bear few small prickles of similar shape and coloration.

I claim:

1. A new and distinct variety of Floribunda rose plant substantially as herein described and illustrated.

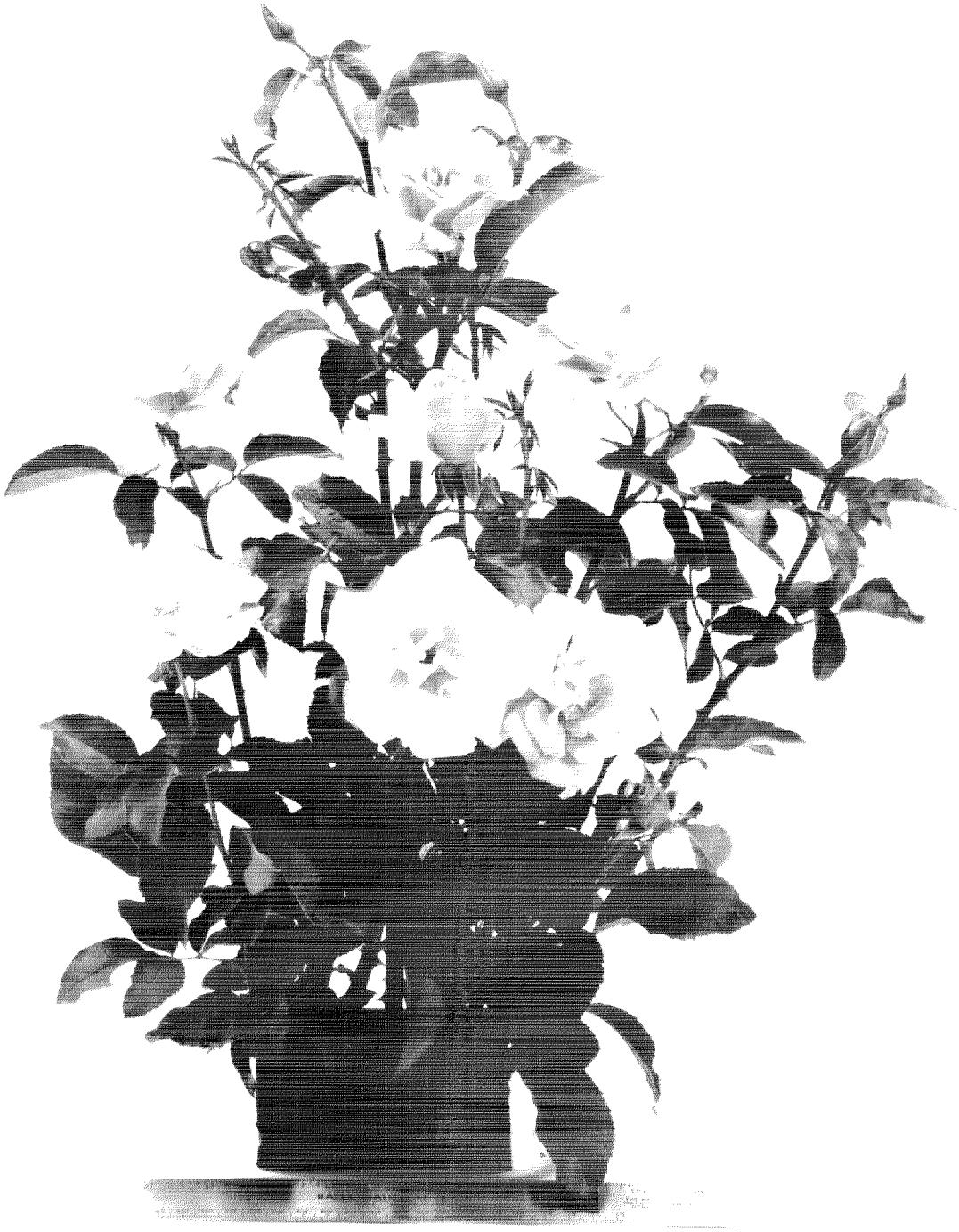

* * * * *